(12) United States Patent
Machhammer et al.

(10) Patent No.: US 7,291,761 B2
(45) Date of Patent: Nov. 6, 2007

(54) PARTIAL DEHYDROGENATION METHOD USING CONTINUOUS HETEROGENEOUS CATALYSIS

(75) Inventors: Otto Machhammer, Mannheim (DE); Goetz-Peter Schindler, Mannheim (DE); Klaus Harth, Altleiningen (DE); Peter Zehner, Ludwigshafen (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 435 days.

(21) Appl. No.: 10/507,001

(22) PCT Filed: Mar. 4, 2003

(86) PCT No.: PCT/EP03/02192

§ 371 (c)(1),
(2), (4) Date: Sep. 8, 2004

(87) PCT Pub. No.: WO03/076370

PCT Pub. Date: Sep. 18, 2003

(65) Prior Publication Data

US 2005/0119515 A1    Jun. 2, 2005

(30) Foreign Application Priority Data

Mar. 13, 2002  (DE) ............................ 102 11 275

(51) Int. Cl.
*C07C 5/327* (2006.01)
*C07C 5/333* (2006.01)

(52) U.S. Cl. .......... 585/658; 585/660; 585/661; 585/662; 585/663

(58) Field of Classification Search ........ 585/658, 585/660–663
See application file for complete search history.

(56) References Cited

U.S. PATENT DOCUMENTS 6,518,476 B1 * 2/2003 Culp et al. .......... 585/655
6,576,804 B1 * 6/2003 Heineke et al. ........ 585/661

FOREIGN PATENT DOCUMENTS

| DE | 199 37 107 | 2/2001 |
|---|---|---|
| DE | 100 28 582 | 12/2001 |
| DE | 100 47 642 | 4/2002 |
| WO | 97/36849 | 10/1997 |
| WO | WO 98/29365 | * 7/1998 |
| WO | 01/96008 | 12/2001 |

* cited by examiner

Primary Examiner—Glenn Caldarola
Assistant Examiner—In Suk Bullock
(74) Attorney, Agent, or Firm—Oblon, Spivak, McClelland, Maier & Neustadt, P.C.

(57) ABSTRACT

A process for the continuous heterogeneously catalyzed partial dehydrogenation of a hydrocarbon in the gas phase and in the presence of molecular oxygen, in which part of the product gas is recirculated to the reaction zone, and a reactor for carrying out such a process.

14 Claims, 2 Drawing Sheets

PARTIAL DEHYDROGENATION METHOD USING CONTINUOUS HETEROGENEOUS CATALYSIS

The present invention relates to a process for the continuous heterogeneously catalyzed partial dehydrogenation of at least one hydrocarbon to be dehydrogenated in the gas phase, in which a reaction gas comprising at least one hydrocarbon to be dehydrogenated is fed continuously to a reaction zone, the reaction gas in the reaction zone is conveyed over at least one fixed catalyst bed over which molecular hydrogen and at least one dehydrogenated hydrocarbon are formed by catalytic (partial) dehydrogenation, at least one gas comprising molecular oxygen is added to the reaction gas before and/or after entry into the reaction zone, the molecular oxygen in the reaction zone oxidizes part of the molecular hydrogen present in the reaction gas to water vapor and a product gas comprising molecular hydrogen, water vapor, the dehydrogenated hydrocarbon or hydrocarbons and the hydrocarbon or hydrocarbons to be dehydrogenated is taken from the reaction zone.

In addition, the present invention provides an apparatus for carrying out the process of the present invention.

The term "dehydrogenated hydrocarbons" used in the present patent application encompasses acyclic and cyclic aliphatic hydrocarbons having one or more C—C double bonds in the molecule. Examples of such aliphatic hydrocarbons are propene, isobutene, 1-butene, 2-butene and butadiene. Thus, dehydrogenated hydrocarbons include, in particular, monounsaturated linear hydrocarbons (n-alkenes) and branched aliphatic hydrocarbons (e.g. isoalkenes) and also cycloalkenes. Furthermore, dehydrogenated hydrocarbons also include alkapolyenes (e.g. dienes and trienes) which have more than one carbon-carbon double bond in the molecule. In addition, hydrocarbon compounds which are obtainable from alkylaromatics such as ethylbenzene or isopropylbenzene by dehydrogenation of the alkyl substituent are also included. These are, for example, compounds such as styrene or α-methylstyrene.

Quite generally, dehydrogenated hydrocarbons are valuable starting compounds for the synthesis of, for example, functionalized, free-radically polymerizable compounds (e.g. acrylic acid from propene or methacrylic acid from isobutene) and their polymerization products. However, they are also suitable for preparing compounds such as methyl tert-butyl ether (downstream product of isobutene which is suitable, for example, as a fuel additive to increase the octane number). However, dehydrogenated hydrocarbons themselves can also be used for polymerization.

It is generally known that dehydrogenated hydrocarbons can be prepared by continuous heterogeneously catalyzed partial dehydrogenation of hydrocarbons to be dehydrogenated in the gas phase (cf., for example, DE-A 10028582, DE-A 10047642, DE-A 19937107 and the references cited in these documents).

As hydrocarbons to be dehydrogenated, it is possible to use, in particular, acyclic and cyclic alkanes and also olefins (whose number of C—C double bonds is to be increased) (for example, the heterogeneously catalyzed partial dehydrogenation of n-butenes to form butadiene).

Thus, the term "hydrocarbons to be dehydrogenated" as used in the present patent application encompasses, in particular, $C_2$-$C_{16}$-alkanes such as ethane, propane, n-butane, isobutane, n-pentane, isopentane, n-hexane, n-heptane, n-octane, n-nonane, n-decane, n-undecane, n-dodecane, n-tridecane, n-tetradecane, n-pentadecane and n-hexadecane.

However, all that which is said in the present text applies particularly to $C_2$-$C_8$-alkanes as hydrocarbons to be dehydrogenated and very particularly preferably to $C_2$-$C_4$-hydrocarbons as hydrocarbons to be dehydrogenated.

Thus, hydrocarbons to be dehydrogenated are for the purposes of the present text especially ethane, propane, n-butane and isobutane, and also 1-butene and 2-butene.

Heterogeneously catalyzed partial dehydrogenations of hydrocarbons to be dehydrogenated require comparatively high reaction temperatures. The conversion which can be achieved is normally limited by the thermodynamic equilibrium. Typical reaction temperatures are from 300 to 700° C. In general, at least one molecule of hydrogen is produced per molecule of dehydrogenated hydrocarbon.

A further characteristic of heterogeneously catalyzed partial dehydrogenations of hydrocarbons to be dehydrogenated is that they are endothermic. The heat of dehydrogenation necessary for achieving a desired conversion therefore has to be introduced into the reaction gas either before and/or during the catalytic dehydrogenation.

In the majority of known processes for the heterogeneously catalyzed partial dehydrogenation of hydrocarbons to be dehydrogenated, the heat of dehydrogenation is generated outside the reactor and introduced from the outside into the reaction gas. However, this requires complicated reactor and process concepts and leads, particularly at high conversions, to steep temperature gradients in the reactor, which generally result in the disadvantage of increased by-product formation.

As an alternative, the heat of dehydrogenation can also be generated directly in the reaction gas itself by addition of molecular oxygen and exothermic combustion of hydrogen which is either formed in the dehydrogenation or additionally introduced to form water vapor. For this purpose, an oxygen-containing gas and, if appropriate, hydrogen is added to the reaction gas before and/or after entry into the reaction zone containing the dehydrogenation catalyst. Either the dehydrogenation catalyst itself (which is the case for most dehydrogenation catalysts) and/or additionally introduced oxidation catalysts generally aid the desired oxidation of hydrogen (cf. DE-A 10028582). Such heat of reaction liberated by means of combustion of hydrogen makes it possible in favorable cases to entirely omit indirect reactor heating and thus allows comparatively simple process concepts and also limited temperature gradients in the reactor in the case of high conversions.

However, a disadvantage of processes for direct generation of heat by means of combustion of hydrogen in the reaction gas is that either they require significant addition of external molecular hydrogen which is comparatively expensive or the selectivity of formation of the dehydrogenated hydrocarbon is not fully satisfactory since the added molecular oxygen burns not only the molecular hydrogen formed during the heterogeneously catalyzed partial dehydrogenation but frequently also part of the hydrocarbon to be dehydrogenated and/or the already dehydrogenated hydrocarbon, which results in an undesirable reduction in the selectivity to the target product.

It is an object of the present invention to provide a process as defined at the outset for the continuous heterogeneously catalyzed partial dehydrogenation of at least one hydrocarbon to be dehydrogenated in the gas phase, which process either no longer has the abovementioned disadvantages and/or suffers from them to a reduced extent.

We found that this object is achieved by a process for the continuous heterogeneously catalyzed partial dehydrogenation of at least one hydrocarbon to be dehydrogenated in the gas phase, in which a reaction gas comprising at least one hydrocarbon to be dehydrogenated is fed continuously to a reaction zone, the reaction gas in the reaction zone is conveyed over at least one fixed catalyst bed over which molecular hydrogen and at least one dehydrogenated hydrocarbon are formed by catalytic (partial) dehydrogenation, at least one gas comprising molecular oxygen is added to the reaction gas before and/or after entry into the reaction zone, the molecular oxygen in the reaction zone oxidizes part of the molecular hydrogen present in the reaction gas to water vapor and a product gas comprising molecular hydrogen, water vapor, the dehydrogenated hydrocarbon or hydrocarbons and the hydrocarbon or hydrocarbons to be dehydrogenated is taken from the reaction zone, wherein the product gas taken from the reaction zone is divided into two substreams of identical composition and one of the two substreams is recirculated as circulated gas to the reaction zone.

The process of the present invention is particularly suitable for the heterogeneously catalyzed partial dehydrogenation of propane to propene, of butane to butene and/or butadiene and of butenes to butadiene.

It differs from catalytic oxydehydrogenation of hydrocarbons in that, in particular, no hydrogen is formed in catalytic oxydehydrogenation. Rather, in that process, the hydrogen split off from the hydrocarbon to be dehydrogenated is split off directly as water ($H_2O$). It therefore generally requires different reaction conditions and other catalysts.

In principle, the process of the present invention can be carried out using all dehydrogenation catalysts which are recommended in the prior art for heterogeneously catalyzed partial dehydrogenations of hydrocarbons to be dehydrogenated in the gas phase with formation of molecular hydrogen.

They can be broadly divided into two groups, namely those which are oxidic in nature (e.g. chromium oxide and/or aluminum oxide) and those which comprise at least one generally comparatively unreactive metal (e.g. platinum) deposited on a generally oxidic support. Lewis-acid dehydrogenation catalysts which have essentially no Brönsted acidity as are described in DE-A 10047642, are preferred according to the present invention.

Suitable dehydrogenation catalysts thus include, in particular, all those dehydrogenation catalysts recommended in DE-A 10060099 (the working example), WO 99/46039, U.S. Pat. No. 4,788,371, EP-A 705136, WO 99/29420, U.S. Pat. No. 5,220,091, U.S. Pat. No. 5,430,220, U.S. Pat. No. 5,877,369, EP-A 117146, DE-A 19937106, DE-A 19937105, DE-A 10047642 and DE-A 19937107.

In particular, the catalysts of Example 1, Example 2, Example 3 and Example 4 of DE-A 19937107 can be used for all variants of the process of the present invention addressed in this text.

These are dehydrogenation catalysts comprising from 10 to 99.9% by weight of zirconium dioxide, from 0 to 60% by weight of aluminum oxide, silicon dioxide and/or titanium dioxide and from 0.1 to 10% by weight of at least one element of main group I or II, an element of transition group III, an element of transition group VIII of the Periodic Table of the Elements, lanthanum and/or tin, with the proviso that the percentages by weight add up to 100% by weight.

The reason for carrying out the process of the present invention over selectively acting catalysts present in the solid state is that cracking (cleavage of C—C) is favored kinetically over dehydrogenation (cleavage of C—H). As a result of the selectively acting catalysts which usually are such that in the absence of oxygen at from 300 to 700° C. (e.g. at 600° C.) they produce significant dehydrogenation (in the case of propane as hydrocarbon to be dehydrogenated, the propylene yield at propane space velocities over the catalysts of, for example, 1000 $h^{-1}$ is at least 30 mol % in a single pass (based on propane used)) and by-products such as methane, ethylene and ethane are formed in only subordinate amounts.

The fixed catalyst bed or beds required in the process of the present invention can be made up of dehydrogenation catalysts having various geometric shapes. Geometries suitable for the process of the present invention are, for example, shapes such as granules, pellets, monoliths, spheres or extrudates (rods, wagonwheels, stars, rings). In the case of extrudates, the length is advantageously from 2 to 15 mm, frequently from 2 to 10 mm, often from 6 to 10 mm, and the diameter of the extrudate cross section is advantageously from 1 to 5 mm, frequently from 1 to 3 mm. In the case of rings, the wall thickness is advantageously from 0.3 to 2.5 mm and their length is from 2 to 15 mm, frequently from 5 to 15 mm and the diameter of their cross section is from 3 to 10 mm. A suitable shaping process is disclosed, for example, in DE-A 10047642 and DE-A 19937107. It is based on that fact that oxidic support materials which have been admixed with concentrated mineral acid (e.g. concentrated nitric acid) can be kneaded comparatively readily and can be converted into a corresponding shaped body by means of a screw extruder or a ram extruder.

The shaped bodies are then dried, calcined and salt solutions are subsequently poured over them in a particular order. The shaped bodies are subsequently dried and calcined again.

In the following description, the discussion will frequently refer specifically to the preferred case of propane dehydrogenation, but the statements made also apply analogously to other dehydrogenatable hydrocarbons.

The reaction zone relevant to the process of the present invention can in principle be achieved in all types of reactor which are known from the prior art for heterogeneously catalyzed partial dehydrogenation of hydrocarbons in the gas phase over fixed-bed catalysts. Typical reaction temperatures are from 200 to 800° C., or from 400 to 650° C. The pressure employed is typically in the range from 0.5 to 10 bar. Typical space velocities of the reaction gas over the catalyst are from 300 to 16 000 $h^{-1}$.

A detailed description of suitable types of reactor is given in, for example, "Catalytica® Studies Division, Oxidative Dehydrogenation and Alternative Dehydrogenation Processes, Study Number 4192 OD, 1993, 430 Ferguson Drive, Mountain View, Calif., 94043-5272 U.S.A.".

One suitable type of reactor is a fixed-bed tube or shell-and-tube reactor. In these, the dehydrogenation catalyst (and any specific hydrogen oxidation catalyst as is disclosed, for example, in U.S. Pat. No. 4,788,371, U.S. Pat. No. 4,886,928, U.S. Pat. No. 5,430,209, U.S. Pat. No. 5,553,0171, U.S. Pat. No. 5,527,979, U.S. Pat. No. 5,563,314 and EP-A 832056) is/are located as a fixed bed in the reaction tube or in a bundle of reaction tubes. The reaction tubes are usually indirectly heated by a gas, e.g. a hydrocarbon such as methane, being burnt in the space surrounding the reaction tubes. It is advantageous to apply this indirect form of heating only to the first approximately 20-30% of the fixed bed and to heat the remaining length of the bed to the required reaction temperature by means of the radiant heat liberated in the combustion. The indirect heating of the reaction gas is, according to the present invention, advantageously combined with the direct heating by combustion with molecular oxygen in the reaction gas.

This combination of the direct introduction of heat according to the present invention with indirect introduction of heat makes it possible to achieve essentially isothermal reactor operation in a comparatively simple form.

Customary internal diameters of the reaction tube(s) are from about 10 to 15 cm. A typical shell-and-tube reactor employed for dehydrogenation has from about 300 to 1000 reaction tubes. The temperature in the interior of the reaction tube is usually in the range from 300 to 700° C., preferably in the range from 400 to 700° C. The pressure employed is usually in the range from 0.5 to 8 bar, frequently from 1 to 2 bar or from 3 to 8 bar. In general, the product gas leaves the reaction tube and thus the reaction zone at a different (higher or lower) temperature compared to the inlet temperature (cf. U.S. Pat. No. 4,902,849, U.S. Pat. No. 4,996,387 and U.S. Pat. No. 5,389,342). Typical space velocities of the hydrocarbon to be dehydrogenated, e.g. propane, over the catalyst are from 500 to 2000 $h^{-1}$ (=standard l/l of catalystor•h).

The process of the present invention can, of course, also be carried out in a moving-bed reactor (in contrast to a fluidized bed, a moving bed will also be regarded as a fixed bed in the present text). For example, the moving bed of dehydrogenation catalyst can be accommodated in a radial-flow reactor. In this, the catalyst moves slowly from the top downward while the reaction gas flows radially. In this case, it is advantageous to employ a plurality of moving-bed reactors connected in series. It is possible, for example, for a gas comprising molecular oxygen to be added to the reaction gas upstream of each reactor so that combustion of this in the respective reactor heats the reaction gas to the reaction temperature.

Depending on which product gas leaving one of the reactors connected in series is divided according to the present invention into two substreams and depending on the reactor to which one substream is recirculated, the reaction zone which is relevant for the purposes of the present invention can be the entire assembly of reactors connected in series or only part thereof (e.g. each reactor on its own). If, for example, four reactors are connected in series and only the product gas leaving the fourth reactor is divided according to the present invention into two substreams and one of the two substreams is recirculated to the first of the preceding reactors, the reaction zone according to the present invention encompasses all four reactors. On the other hand, if only the product gas leaving the first of the reactors connected in series is divided according to the present invention into two substreams and one of the two substreams is recirculated to the first reactor, the reaction zone according to the present invention is only the first reactor.

Dehydrogenation catalysts used according to the present invention in moving-bed reactors advantageously have a spherical shape. The pressure employed is typically from 2 to 5 bar. The reaction temperatures are typically from 550 to 660° C. The catalyst charge can in this case, as also in the case of all other reactors described in this text as suitable for the process of the present invention, be made up of a mixture of dehydrogenation catalyst and $H_2$ oxidation catalyst, as recommended, for example, by EP-A 832056.

In another embodiment of the process of the present invention, the heterogeneously catalyzed dehydrogenation is carried out in a tray reactor. This contains one or more physically separate catalyst beds arranged in succession. The number of catalyst beds can be from 1 to 20, advantageously from 2 to 8, and in particular from 4 to 6. The reaction gas preferably flows radially or axially through the catalyst beds.

In the simplest case, the catalyst beds are located in a shaft furnace reactor either axially or in the annular gaps of concentric cylindrical gratings. One shaft furnace reactor corresponds to one tray. It is possible for the process of the present invention to be carried out in a single shaft furnace reactor.

If no gas comprising molecular oxygen has been added to the reaction gas before and/or after entry into the reaction zone in the process of the present invention, the reaction gas is advantageously subjected to intermediate heating on its way from one catlayst bed to the next catalyst bed in the tray reactor, e.g. by passing it over heat exchanger ribs heated by means of hot gases or by passing it through tubes heated by hot combustion gases.

In the process of the present invention, intermediate heating as indicated above is carried out at least partly by the direct route. For this purpose, a limited amount of a gas comprising molecular oxygen is added to the reaction gas either before it flows through the first catalyst bed and/or between the subsequent catalyst beds.

Thus, molecular hydrogen added beforehand to the reaction gas and/or formed during the dehydrogenation is burnt to a limited extent in at least one, possibly in all, catalyst beds. The heat of reaction liberated in this way thus makes it possible for the heterogeneously catalyzed hydrocarbon dehydrogenation of the present invention to be carried out essentially autothermally.

In one embodiment of the invention, intermediate introduction of oxygen-containing gas may be carried out before each tray of the tray reactor. In a further embodiment of the process of the present invention, oxygen-containing gas is fed in before each tray apart from the first tray. In a further embodiment of the process of the present invention, a bed of specific oxidation catalyst suitable for oxidation of $H_2$ is present downstream of each oxygen introduction point, followed by a bed of dehydrogenation catalyst. If necessary, external molecular hydrogen can be additionally fed in upstream of each tray.

However, it is an important aspect of the present invention that the process of the present invention does not necessarily require introduction of external molecular hydrogen (this refers to molecular hydrogen which is neither a constituent of the circulating gas recirculated to the reaction zone nor is formed in the reaction zone itself).

The dehydrogenation temperature in the tray reactor is generally from 400 to 800° C. and the pressure is generally from 0.2 to 10 bar, preferably from 0.5 to 4 bar and particularly preferably from 1 to 2 bar. The total space velocity of gas (GHSV) is generally from 500 to 2000 $h^{-1}$, and in high-load operation even up to 16 000 $h^{-1}$, frequently from 4000 to 16 000 $h^{-1}$.

The hydrocarbons to be dehydrogenated in the process of the present invention do not have to be pure substances. Rather, the hydrocarbon to be dehydrogenated can further comprise other dehydrogenatable gases. In the case of propane, these can be methane, ethane, ethylene, propene, butanes, butenes, propene, acetylene, $H_2S$ or pentanes.

The gas comprising molecular oxygen which is to be added to the reaction gas before and/or after entry into the reaction zone in the process of the present invention can either be pure molecular oxygen or a mixture with inert gases such as $CO_2$, $N_2$ or noble gases. Air is normally used advantageously as gas comprising molecular oxygen.

Correspondingly, any molecular hydrogen added externally to the reaction zone in the process of the present invention can be added in pure form or as a mixture diluted with inert gas.

Since the heterogeneously catalyzed partial dehydrogenation according to the present invention of at least one hydrocarbon to be dehydrogenated proceeds with an increase in volume, the conversion can be increased by reducing the partial pressure of the reactants. This can be achieved in a simple manner by, for example, carrying out the dehydrogenation at a subatmospheric pressure and/or by mixing in an inert gas, which is why the abovementioned inert gases are thoroughly desirable in the process of the present invention.

As mentioned above, inert gases suitable for the process of the present invention are, for example, nitrogen, steam, carbon dioxide and noble gases such as He, Ne or Ar. Preferred inert diluents are ones which are changed chemically to an extent of less than 5 mol %, particularly preferably less than 3 mol % and even more preferably less than 1 mol %, under the reaction conditions of the process of the present invention. All diluents mentioned can be used in the process of the present invention either as such or in the form of various mixtures. However, diluent gases used can also be gases which react exothermically with molecular oxygen more rapidly than does the dehydrogenated hydrocarbon(s) and/or hydrocarbon(s) to be dehydrogenated under the given boundary conditions.

However, the process of the present invention can in principle also be carried out without the presence of inert gases having a diluent effect, i.e. the process of the present invention can also be a process in which the reaction gas fed to the reaction zone can consist exclusively of the hydrocarbon or hydrocarbons to be dehydrogenated. The gas comprising molecular oxygen which is required according to the present invention is in these cases fed in only along the reaction path of the reaction zone. However, it can, according to the present invention, also be added to the reaction gas before the latter enters the reaction zone. In this case, the reaction gas may thus comprise the hydrocarbon or hydrocarbons to be dehydrogenated and only molecular oxygen or molecular oxygen and one or more inert gases. Of course, gas comprising molecular oxygen can be added to the reaction gas in the process of the present invention either before the reaction gas enters the reaction zone or along the reaction path in the reaction zone.

According to the present invention, preference is given to adding the total amount of gas comprising molecular oxygen to the reaction gas before it enters the reaction zone. Here, as quite generally in the process of the present invention, it is advantageous for external molecular hydrogen to be added to the reaction gas neither before the latter enters the reaction zone nor along the reaction path.

In general, the amount of molecular oxygen added to the reaction gas before it enters the reaction zone is, based on the total amount of the hydrocarbon to be dehydrogenated (e.g. propane), from 0.001 to 0.5 mol/mol, preferably from 0.005 to 0.2 mol/mol and particularly preferably from 0.05 to 0.2 mol/mol. The higher ratios are preferably employed for higher propane conversions. According to the present invention, the amount of molecular oxygen added to the reaction gas is advantageously calculated so that virtually all the heat required for the heterogeneously catalyzed dehydrogenation of the hydrocarbon or hydrocarbons is generated along the reaction path by combustion of molecular hydrogen. In particular embodiments, the heat generated by combustion of molecular hydrogen with molecular oxygen can also be greater than or less than the heat required for the dehydrogenation of the hydrocarbon.

According to the present invention, it is advantageous for the total amount of inert gas required (excluding inert gas formed in the reaction zone by chemical reaction) likewise to be added to the reaction gas before it enters the reaction zone, i.e. no intermediate introduction of inert gas is carried out according to the present invention.

Steam is advantageously used as inert diluent gas or at least part thereof in the process of the present invention. Apart from its diluent action, steam has the further advantage that it generally reduces carbon deposits on the catalysts used in the process of the present invention, since the steam normally reacts with such carbon deposits according to the principle of the water gas reaction.

It is likewise preferred according to the present invention for no intermediate introduction of steam to be carried out, but for the amount of steam to be added to be added all at once to the reaction gas before it enters the reaction zone. The ratio of steam to the hydrocarbon or hydrocarbons to be dehydrogenated in the reaction gas before it enters the reaction zone is therefore generally from 0 to 10 mol/mol, frequently from 0.1 to 10 mol/mol and preferably from 0.1 to 5 mol/mol.

Since the molecular oxygen required in the process of the present invention is normally added as a constituent of air, the reaction gas normally also contains molecular nitrogen as diluent gas before it enters the reaction zone, i.e. the reaction gas fed to the reaction zone in the process of the present invention will generally contain steam and nitrogen as inert diluent gases.

A feature of the process of the present invention is that the product gas taken from the reaction zone, which comprises molecular hydrogen, water vapor, the hydrocarbon or hydrocarbons to be dehydrogenated and the dehydrogenated hydrocarbon or hydrocarbons, is divided into two substreams of identical composition and one of the two substreams is recirculated as reaction gas to the reaction zone. This recirculation can be carried out either in the form of intermediate introductions or at the point where the reaction gas enters the reaction zone. According to the present invention, it is preferably carried out exclusively at the point where the reaction gas enters the reaction zone. The reaction gas itself is, in the process of the present invention, normally fed into the reaction zone at only one point and not via additional intermediate points of introduction.

The sum of the reaction gas fed to the reaction zone and recirculated circulating gas fed in at the point where the reaction gas enters the reaction zone will be referred to as inlet gas in the present text.

The advantageous nature of the process of the present invention is attributed to the product gas recirculated to the reaction zone still containing molecular hydrogen formed during the heterogeneously catalyzed partial dehydrogenation, which offers the opportunity of entirely omitting the addition of external hydrogen in the process of the present invention while nevertheless achieving the advantages of the combustion of hydrogen. Particularly when the circulating gas recirculated to the reaction zone is a constituent of the inlet gas, the inlet gas comprises, right from the beginning, molecular hydrogen for combustion purposes which does not come from an expensive external source.

The combustion of the molecular hydrogen present in the circulating gas leads to elimination of hydrogen from the dehydrogenation equilibrium, which increases the thermodynamically possible dehydrogenation conversion under otherwise identical conditions. Furthermore, the recirculation of circulating gas according to the present invention results in increased selectivity to the formation of dehydrogenated hydrocarbon. This is particularly true when the hydrocarbon to be dehydrogenated is propane. A reason for this selectivity increase could be that the hydrocarbon which has already been dehydrogenated once which is recirculated in the circulating gas to the reaction zone surprisingly acts largely as an inert gas in respect of the comparatively specific catalytic dehydrogenation sought and the combustion of hydrogen.

According to the present invention, it is advantageous to recirculate at least 10% or 20% of the product gas taken from the reaction zone to the reaction zone. However, it is advantageous according to the present invention for the proportion of the product gas taken from the reaction zone which is recirculated as circulating gas to the reaction zone to be not more than 90% or 80%, i.e. the substream of the product gas taken from the reaction zone which is recirculated as circulating gas to the reaction zone in the process of the present invention amounts to, for example, from 20 to 80% or from 30 to 70% or from 40 to 60% or else 50% of the product taken off. A proportion of from 50 to 70% is particularly advantageous.

If, in the process of the present invention, the reaction gas and the circulating gas are, in a preferred manner, fed into the reaction zone at only one point so that the inlet gas contains the total amount of both molecular oxygen and molecular hydrogen fed into the reaction zone, the overall heterogeneously catalyzed partial dehydrogenation according to the present invention of at least one hydrocarbon to be dehydrogenated can be carried out either endothermically, autothermally (the net reaction enthalpy over the reaction zone is essentially zero) or exothermically, based on a single pass of the inlet gas mixture through the reaction zone, by means of appropriate choice of the molar ratio of molecular oxygen to molecular hydrogen in the inlet gas. Autothermal to slightly exothermal operation is preferred according to the present invention. In this case, it is regarded as advantageous according to the present invention for the abovementioned molar ratio of molecular oxygen present in the inlet gas to molecular hydrogen present in the inlet gas to be 1:1 or less, particularly preferably 1:2 or less. If the abovementioned ratio is set to a value greater than 1:2 and more than 90% of the product gas taken from the reaction zone is recirculated as circulating gas, the thermodynamic control of the heterogeneously catalyzed partial dehydrogenation of the present invention can largely be overcome and conversions in the range from 80 to 90 mol %, based on a single pass of the reaction gas, can be achieved. In general, the overall reaction is then exothermic.

If required, the inlet gas can be preheated before it enters the reaction zone.

Without any particular measures, the process of the present invention can be operated so that a conversion of the hydrocarbon to be dehydrogenated (e.g. propane or butane) of from $\geqq 5$ mol % to $\leqq 70$ mol % is achieved in a single pass of the reaction gas through the reaction zone.

The choice of the conversion is based, in particular, on the subsequent use of the part of the product gas taken from the reaction zone which is not recirculated as circulating gas to the reaction zone. This product output can, for example, be worked up in a known manner by separating off constituents other than hydrocarbons present in it, for example by selective absorption of the hydrocarbons present in an organic solvent, e.g. as described in DE-A 10 028 582, and/or by rectification, and separating the remaining mixture of hydrocarbon to be dehydrogenated and dehydrogenated hydrocarbon in a splitter (e.g. in the case of propane as hydrocarbon to be dehydrogenated) and recirculating the hydrocarbon to be dehydrogenated to the dehydrogenation as constituent of the reaction gas, while passing the dehydrogenated hydrocarbon which has been separated off to a further target reaction. In this case, the process of the present invention is advantageously carried out at relatively high hydrocarbon conversions (typically from 35 to 60 mol %).

However, the process of the present invention is frequently coupled with a process for preparing partial oxidation products and/or partial ammoxidation products or with a process for preparing alkylation products, Diels-Alder adducts, oxychlorination products and methathesis products of the dehydrogenated hydrocarbon(s) present in the product gas taken from the reaction zone of the process of the present invention (e.g. propene or isobutene), as is recommended, for example, in U.S. Pat. No. 3,161,670, EP-A 117 146, DE-A 33 13 573, DE-A 10 028 582, DE-A 10 131 297 or in DE-A 10 148 575, DE-A 10 148 577, DE-A 10 206 954, DE-A 10 159 615, DE-A 10 118 634, DE-A 10 130 958 and DE-A 10 160 726. In these cases, conversions of from $\geqq 5$ mol % to $\leqq 30$ mol % or $\leqq 25$ mol %, frequently about 20 mol %, are sufficient in the dehydrogenation process of the present invention.

For this purpose, part or all of the constituents other than the hydrocarbon or hydrocarbons to be dehydrogenated (e.g. propane, n-butane or isobutane) and the dehydrogenated hydrocarbon or hydrocarbons (e.g. propene, n-butene or isobutene) present in the substream (product gas mixture A) of the product gas taken from the reaction zone in the process of the present invention which is not recirculated to the reaction zone are separated off from this substream, if appropriate in a separation zone, to give a product gas mixture A' and either the product gas mixture A or the product gas mixture A' is used as feed for one of the abovementioned downstream reactions such as a heterogeneously catalyzed oxidation and/or ammoxidation zone in which the dehydrogenated hydrocarbon or hydrocarbons present is, for example, subjected to partial oxidation and/or ammoxidation by means of molecular oxygen to form a product mixture B which comprises as target product at least one partial oxidation and/or ammoxidation product (e.g. acrylic acid, methacrylic acid, acrolein, acrylonitrile, etc.) of the dehydrogenated hydrocarbon or hydrocarbons.

Target product is subsequently separated off from the product gas mixture B in a work-up zone C and at least part of the unreacted hydrocarbon or hydrocarbons to be dehydrogenated present in the remaining product gas mixture B is recirculated as constituent of a second circulating gas to the reaction zone of the dehydrogenation process of the present invention as source for the reaction gas.

This second circulating gas will generally comprise the hydrocarbon to be hydrogenated together with inert and/or reactive diluent gases such as oxygen compounds, methane, ethane, ethylene, higher hydrocarbons, water vapor, $N_2$, CO, $CO_2$ and possibly molecular oxygen.

In the case of the process of the present invention being coupled in this way with a heterogeneously catalyzed partial oxidation and/or ammoxidation of the dehydrogenated hydrocarbon or hydrocarbons, it is advantageous to carry out the oxidation and/or ammoxidation process using an excess of molecular oxygen, relative to the stoichiometrically required amount for the oxidation and/or ammoxidation. The work-up in the work-up zone C is then advantageously carried out so that this excess of molecular oxygen essentially remains in the second circulating gas. This second circulating gas comprising molecular oxygen can then be employed as constituent of the reaction gas for the process of the present invention as source (preferably sole source) of the molecular oxygen required in the process of the present invention. This applies particularly when the hydrocarbon to be dehydrogenated is propane and the partial oxidation product of the dehydrogenated hydrocarbon propene is acrolein and/or acrylic acid.

If the second circulating gas comprising molecular oxygen which is recirculated to the reaction zone of the process of the present invention further comprises CO, oxygen compounds such as acrolein, acrylic acid, formaldehyde, acetic acid and/or ethylene oxide, these can be oxidized to, for example, $CO_2$ and $H_2O$ by means of the molecular oxygen either beforehand and/or in this reaction zone, likewise in the presence of a heterogeneous catalyst. The heat of reaction liberated in this oxidation can likewise be employed for the purpose of heating the reaction gas.

It is advantageous according to the present invention for the reaction zone of the process of the present invention to comprise only one catalyst bed in which the catalyst used is a catalyst as described in Example 1, Example 2, Example 3 or Example 4 of DE-A 19 937 107 or as described in the working example of DE-A 10 060 099.

If the hydrocarbon to be dehydrogenated is propane and the dehydrogenated hydrocarbon is propene, then the inlet gas mixture can be composed of:

a) from 50 to 70% of the product gas taken from the (dehydrogenation) reaction zone (first circulating gas), which usually has the following composition:

| | | | |
|---|---|---|---|
| 0-1% | by volume of methane, | 0-60% | by volume of $H_2O$, |
| 0-1% | by volume of ethane, | 0-1% | by volume of $C_{4+}$-hydrocarbon, |
| 0-1% | by volume of ethene, | 0-2% | by volume of $CO_2$, |
| 1-10% | by volume of $H_2$, | 0-2% | by volume of $O_2$, |
| 1-20% | by volume of propene, | 10-40% | by volume of propane, |
| 0-1% | by volume of CO, | balance to 100% | by volume: essentially nitrogen; | b) a second circulating gas which comes from the heterogeneously catalyzed partial oxidation to acrolein and/or acrylic acid of the propene present in the part of the product gas taken from the dehydrogenation reaction zone which is not recirculated directly to the dehydrogenation reaction zone; this second circulating gas usually has the following composition:

| | | | |
|---|---|---|---|
| 0-1% | by volume of methane, | 0-1% | by volume of CO, |
| 0-5% | by volume of $H_2O$, | 0-3% | by volume of $CO_2$, |
| 0-1% | by volume of ethene, | 0-10% | by volume of $O_2$, |
| 0-1% | by volume of ethane, | 10-40% | by volume of propane, |
| 0-1% | by volume of hydrogen, | 0-1% | by volume of $C_{4+}$-hydrocarbons, |
| 0-1% | by volume of propene, | balance to 100% | by volume: essentially nitrogen; | c) fresh propane and fresh steam.

Introduction of further gases into the reaction zone is not necessary according to the present invention.

The volume ratios here are advantageously:
first circulating gas: second circulating gas: fresh propane: fresh steam=10-30:10-30:1:0.1-5.

The above volume ratios are preferably 20:20:1:1. The heterogeneously catalyzed dehydrogenation is preferably carried out essentially autothermally at from 450° C. to 650° C. and a pressure of from 1 bar to 3 bar. The space velocity of inlet gas over the dehydrogenation catalyst is advantageously from 2000 to 20 000 standard l/l of cat.•h.

The preferred catalyst geometry is extrudates having a length of from 2 mm to 10 mm and a diameter of the cross section of from 1 mm to 4 mm.

The used catalyst can be regenerated as described in DE-A 10 028 582. In the case of pronounced deactivation, the regeneration procedure can be repeated a number of times to effectively restore its original performance. The regeneration procedure comprises a regeneration step using pure molecular hydrogen or molecular hydrogen diluted with inert gas. To restrict the amount of hydrogen required for this regeneration step, it is advantageous in practice either to circulate the regeneration hydrogen or, particularly simply, to allow it to remain for a relatively long period over the deactivated catalyst. As reactor for the dehydrogenation, it is possible to employ a simple shaft reactor. The partial oxidation can then be carried out as described in the above-cited documents of the prior art (in particular DE-A 10 311 297 and DE-A 10 028 582). Preference is given to separating off all constituents other than propane and propene from the product gas mixture A before it is used for the partial oxidation.

In the process of the present invention, the recirculation of circulating gas to the reaction zone is usually carried out by means of a compressor located outside the reaction zone.

However, this circulation of gas can be achieved particularly elegantly in a jet pump circulation reactor.

Figure 1:
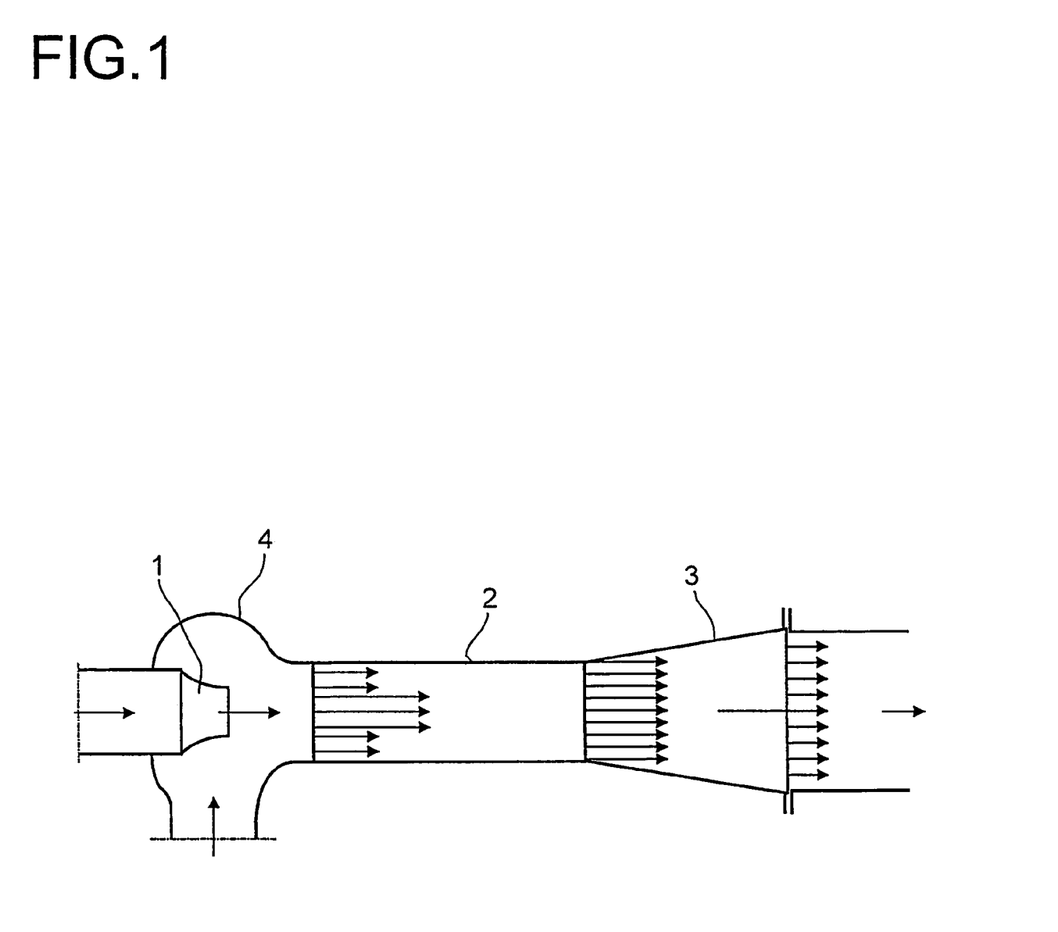
FIG. 1 is shows a schematic sketch of a jet pump.

Such a reactor comprises the catalyst charge and at least one jet pump (FIG. 1 shows a schematic sketch of a jet pump). This pump comprises a driving nozzle (1), a mixing tube (2), a diffuser (3) and a suction section (4). The numerals in brackets refer to FIG. 1.

Figure 2:
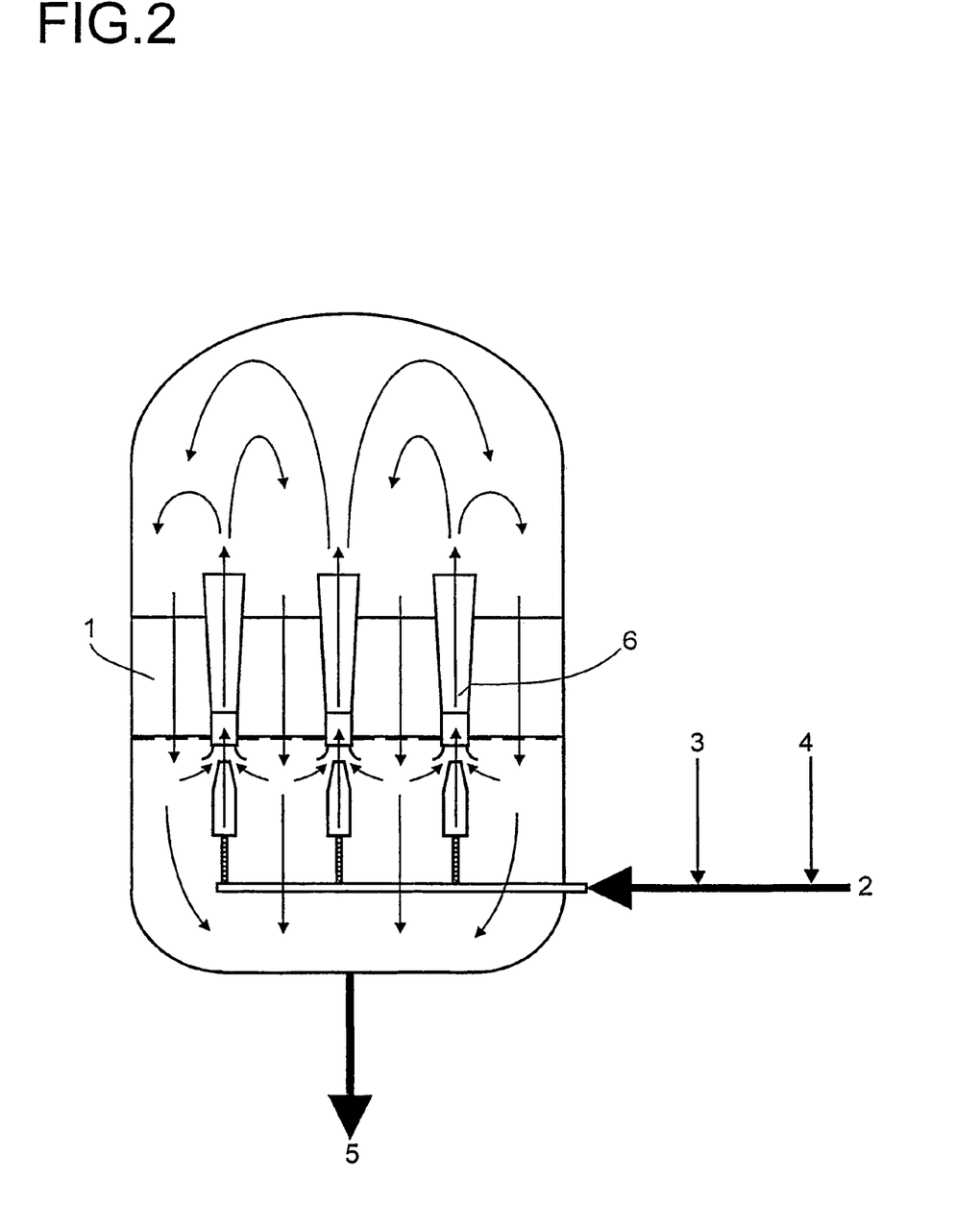
FIG. 2 shows an example of a jet pump circulation reactor.

A driving jet is expanded into the mixing tube through the driving nozzle in the transport direction. This generates a reduced pressure in the suction section so that the gas surrounding the suction section is drawn in and is, while simultaneously being mixed with the driving jet, transported through the mixing tube via the diffuser and discharged. In the process of the present invention, the driving jet is advantageously formed by the reaction gas to be fed into the reaction zone. Downstream of the diffuser, the direction of transport is reversed and the reaction gas is fed to the catalyst charge. A substream of the product gas leaving the catalyst charge is drawn in via the suction section, mixed with reaction gas in the mixing tube and discharged via the diffuser as inlet gas mixture. The remainder of the product gas is conveyed out of the reactor. The term "jet pump" used in the present text also includes ejectors. An example of a suitable configuration of a jet pump circulation reactor is shown in FIG. 2. In FIG. 2, the numerals have the following meanings:

1=catalyst bed; 2=e.g. propane; 3=e.g. air; 4=e.g. steam; 5=product gas; 6=jet pumps.

This is a jet pump circulation reactor of the type in which the suction section is located on one side of the catalyst charge and the diffuser is located on the other side. In the case of jet pumps located in the interior of the reactor, it can be advantageous to configure the suction section so that it can be closed off. This can be advantageous for, in particular, regeneration of the catalyst charge. During such a procedure, the driving jet is formed by regeneration gas while the suction section is closed. However, it can also be open. It goes without saying that the jet pump or pumps of the jet pump circulation reactor can also be located outside the reactor chamber in which the catalyst charge is present.

A further advantage which may be expected in the process of the present invention is an increased operating life of the catalyst charge compared to a process operated without recirculation of circulating gas to the reaction zone.

EXAMPLES AND COMPARATIVE EXAMPLES

1. Setting up the Dehydrogenation Reactor ready for Operation

A solution of 11.993 g of $SnCl_2 \cdot 2\,H_2O$ and 7.886 g of $H_2PtCl_6 \cdot 6\,H_2O$ in 600 ml of ethanol was poured over 1000 g of a crushed $ZrO_2 \cdot SiO_2$ mixed oxide.

The mixed oxide had a $ZrO_2/SiO_2$ weight ratio of 95:5. The mixed oxide was manufactured by Norton (USA).

The mixed-oxide had the following specification: type AXZ 311070306, lot no. 2000160042, sieve fraction: 1.6 to 2 mm, BET surface area: 86 $m^2/g$, pore volume: 0.28 ml/g (measured by mercury porosimetry).

The supernatant ethanol was taken off under a waterpump vacuum (20 mbar) on a rotary evaporator at a waterbath temperature of 40° C. The solid was subsequently dried under static air for 15 hours at 100° C. and subsequently calcined under static air at 560° C. for 3 hours. A solution of 7.71 g of $CsNO_3$, 13.559 g of $KNO_3$ and 98.33 g of $La(NO_3)_3 \cdot 6\,H_2O$ in 2500 ml of $H_2O$ was then poured over the dried solid. The supernatant water was taken off under a waterpump vacuum (20 mbar) on a rotary evaporator at a water bath temperature of 85° C. The solid was subsequently dried under static air for 15 hours at 100° C. and subsequently calcined under static air at 560° C. for 3 hours.

The catalyst precursor obtained in this way had a composition of $Pt_{0.3}Sn_{0.6}Cs_{0.5}K_{0.5}La_{3.0}$ (weight ratios) on $(ZrO_2)_{95} \cdot (SiO_2)_5$ (weight ratio).

A vertical tube reactor (reactor length: 800 mm; wall thickness: 2 mm; internal diameter: 20 mm; reactor material: internally alonized (i.e. coated with aluminum oxide) steel tube; heating: electric (furnace from HTM Reetz, LOBA 1100-28-650-2) on a length of 650 mm in the middle part of the length of the reactor; length of the catalyst bed: 75 mm; position of the catalyst bed: in the middle part of the length of the tube reactor; filling of the remaining reactor volume above and below with steatite spheres (inert material) having a diameter of 4-5 mm, supported at the bottom on a catalyst rest) was charged with 20 ml of the catalyst precursor obtained.

The reaction tube was subsequently supplied with 9.3 standard l/h of hydrogen for 30 minutes at an external wall temperature setting along the heating zone of 500° C. (based on a tube through which an identical inert gas stream was passed). The stream of hydrogen was subsequently replaced, at the same wall temperature, firstly by 23.6 standard l/h of a stream consisting of 80% by volume of nitrogen and 20% by volume of air for 30 minutes and then by an identical stream of pure air for 30 minutes. While maintaining the wall temperature, an identical stream of $N_2$ was passed through the reactor for 15 minutes and the catalyst was finally reduced again by means of 9.3 standard l/h of hydrogen for 30 minutes. This concluded the activation of the catalyst precursor.

2. Comparative Example 1

A dehydrogenation reactor which had been made ready for operation as described under 1. was supplied at the same temperature setting (500° C. wall temperature based on inert gas being passed through it) with a mixture of 20 standard l/h of crude propane and 20 g/h of water vapor as reaction gas. The crude propane was metered by means of a mass flow regulator from Brooks, while the water was initially introduced in liquid form into a vaporizer by means of an HPLC pump 420 from Kontron, vaporized in the vaporizer and then mixed with the crude propane. The temperature of the reaction gas was 150° C.

The outlet pressure of the reactor was set to 1.5 bar absolute by means of a pressure regulator (from REKO) located at the reactor outlet.

The product gas which had been depressurized to atmospheric pressure downstream of the pressure regulator was cooled, resulting in the water vapor present condensing out. The remaining uncondensed gas was analyzed by GC (HP 6890 with Chem-Station, detectors: FID, WLD, separation columns: $Al_2O_3/KCl$ (Chrompack), Carboxen 1010 (Supelco)). The reaction gas was also analyzed in an analogous fashion.

Table 1 below reports the results achieved as a function of the time of operation. Here, the percent by volume figures are based on "dry" gas, i.e. the amount of water vapor present was disregarded in all cases.

TABLE 1

|  | Reaction gas % by volume | Product gas (after 1 h) % by volume | Product gas (after 9 h) % by volume |
| --- | --- | --- | --- |
| Propane | 99.99 | 64.25 | 62.81 |
| Propene | 0.0096 | 16.61 | 16.49 |
| $H_2$ | 0 | 18.74 | 20.33 |
| $O_2$ | 0 | 0 | 0 |
| $N_2$ | 0 | 0.068 | 0.065 |
| Methane | 0 | 0.040 | 0.033 |
| Ethane | 0.0017 | 0.118 | 0.108 |
| Ethene | 0 | 0.019 | 0.019 |
| CO | 0 | 0.019 | 0.014 |
| $CO_2$ | 0 | 0.129 | 0.124 |

These values correspond to a propane conversion based on a single pass of the reaction gas of 20.8 mol % and a selectivity of propene formation of 99.1 mol %.

Comparative Example 2

The boundary conditions of Comparative Example 1 were maintained, but an additional 7.5 standard l/h of air were added to the reaction gas and the experiment was subsequently continued. The space velocity of propane through the catalyst bed corresponded to that in Comparative Example 1. Table 2 below reports the results achieved as a function of the time of operation (time from the change to the new reaction conditions). The % by volume figures are once again based on "dry" gas.

TABLE 2

|  | Reaction gas % by volume | Product gas (after 3 h) % by volume | Product gas (after 20 h) % by volume |
|---|---|---|---|
| Propane | 73.16 | 45.43 | 46.49 |
| Propene | 0.007 | 14.40 | 14.03 |
| $H_2$ | 0 | 17.56 | 17.01 |
| $O_2$ | 5.34 | 0 | 0 |
| $N_2$ | 21.50 | 19.28 | 18.97 |
| Methane | 0 | 0.16 | 0.24 |
| Ethane | 0.0012 | 0.20 | 0.22 |
| Ethene | 0 | 0.05 | 0.07 |
| CO | 0 | 0.16 | 0.16 |
| $CO_2$ | 0 | 2.77 | 2.81 |

Comparison with Table 1 shows that the presence of atmospheric oxygen results both in an increase in $CO_x$ formation and in increased formation of cracking products (methane, ethane and ethene). Both reduce the selectivity of propene formation. The latter was, based on a single pass of the reaction gas and a propane conversion of 24.6 mol %, determined as 91.4 mol %.

Example

The boundary conditions of Comparative Example 2 were maintained, but 422 l/h of the product gas which had been cooled to 150° C. were recirculated to the inlet of the reactor (by means of a diaphragm compressor from KNF Neuberger, P≈1.5 bar) and mixed there with the reaction gas as described in Comparative Example 2 to form the inlet gas fed to the catalyst bed. The amount of circulated gas was set by means of an orifice plate measurement (from Rosemount, orifice diameter: 1.3 mm) coupled with the membrane compressor. To avoid condensation of water, the membrane compressor, the orifice plate measurement and the circulating gas lines were heated to 150° C. by means of heating tapes. The space velocity of propane was kept the same as in Comparative Example 2. The part of the product gas which was not recirculated to the reaction zone was analyzed as described. Table 3 below reports the results achieved as a function of the time of operation (time from change to the new reaction conditions). The volume % figures are once again based on "dry" gas.

TABLE 3

|  | Inlet gas % by volume | Product gas (after 3 h) % by volume | Product gas (after 20 h) % by volume |
|---|---|---|---|
| Propane | 73.08 | 60.15 | 57.97 |
| Propene | 0.007 | 13.10 | 14.51 |
| $H_2$ | 0 | 5.36 | 6.94 |
| $O_2$ | 5.36 | 0 | 0 |
| $N_2$ | 21.55 | 20.73 | 19.93 |
| Methane | 0 | 0.04 | 0.04 |
| Ethane | 0.0009 | 0.12 | 0.13 |
| Ethene | 0 | 0.12 | 0.11 |
| CO | 0 | 0.01 | 0.02 |
| $CO_2$ | 0 | 0.37 | 0.36 |

Comparison of Table 3 with Table 2 shows that operation with recirculation of gas according to the present invention suppresses the increase in $CO_x$ formation in Comparative Example 2 caused by addition of air and the formation of cracking products (methane, ethane and ethene) to a level, based on propene formed, which corresponds almost to that in Comparative Example 1 which was carried out with exclusion of oxygen. This displays an increase in selectivity of propene formation compared to Comparative Example 2. Furthermore, the numerical values for the hydrogen content compared to Table 2 show that the recirculated hydrogen has largely been oxidized selectively by the atmospheric oxygen. Based on a single pass of the inlet gas, the selectivity of propene formation was 98.0 mol % at a propane conversion of 20.3 mol %.

We claim:

1. A process for the continuous heterogeneously catalyzed partial dehydrogenation of at least one hydrocarbon to be dehydrogenated in the gas phase, in which
   a reaction gas comprising at least one hydrocarbon to be dehydrogenated is fed continuously to a reaction zone,
   the reaction gas in the reaction zone is conveyed over at least one fixed catalyst bed over which molecular hydrogen and at least one dehydrogenated hydrocarbon are formed by catalytic (partial) dehydrogenation,
   at least one gas comprising molecular oxygen is added to the reaction gas before and/or after entry into the reaction zone,
   the molecular oxygen in the reaction zone oxidizes part of the molecular hydrogen present in the reaction gas to water vapor, and
   a product gas comprising molecular hydrogen, water vapor, the dehydrogenated hydrocarbon or hydrocarbons and the hydrocarbon or hydrocarbons to be dehydrogenated is taken from the reaction zone,
   wherein the product gas taken from the reaction zone is divided into two substreams of identical composition and one of the two substreams is recirculated as circulated gas to the reaction zone.

2. A process as claimed in claim 1, wherein the fixed catalyst bed or beds comprise dehydrogenation catalysts comprising from 10 to 99.9% by weight of zirconium dioxide, from 0 to 60% by weight of aluminum oxide, silicon dioxide and/or titanium dioxide and from 0.1 to 10% by weight of at least one element of main group I or II, an element of transition group III, an element of transition group VIII of the Periodic Table of the Elements, lanthanum and/or tin, with the proviso that the percentages by weight add up to 100% by weight.

3. A process as claimed in claim 1, wherein the fixed catalyst bed comprises catalyst extrudates and/or catalyst rings.

4. A process as claimed in claim 1, wherein the hydrocarbon to be dehydrogenated is propane and/or butane.

5. A process as claimed in claim 1, wherein at least one gas comprising molecular oxygen is added to the reaction gas exclusively before it enters the reaction zone.

6. A process as claimed in claim 1, wherein air is added as at least one gas comprising molecular oxygen.

7. A process as claimed in claim 1, wherein apart from the circulating gas no further gas comprising molecular hydrogen is introduced into the reaction zone.

8. A process as claimed in claim 1, wherein the reaction gas fed to the reaction zone contains water vapor.

9. A process as claimed in claim 1, wherein the substream of the product gas taken from the reaction zone which is recirculated as circulating gas to the reaction zone amounts to from 20 to 80% of the product gas taken off.

10. A process as claimed in claim 1, wherein the substream of the product gas which is not recirculated as circulating gas to the reaction zone is, if appropriate after part of the components present therein other than the dehydrogenated hydrocarbon or hydrocarbons have been separated off, used for the partial oxidation and/or amoxidation of the dehydrogenated hydrocarbon.

11. A process as claimed in claim 1, wherein the reaction gas further comprises an added second circulating gas which comprises the hydrocarbon or hydrocarbons to be dehydrogenated and comes from a partial oxidation and/or amoxidation of the dehydrogenated hydrocarbon.

12. A process as claimed in claim 11, wherein the second circulating gas which comes from the partial oxidation and/or amoxidation of the dehydrogenated hydrocarbon and is recirculated to the reaction zone is the only gas comprising molecular oxygen which is added to the reaction zone.

13. A process as claimed in claim 1, carried out in a jet pump circulation reactor.

14. A reactor comprising at least one catalyst bed which is suitable for the catalytic dehydrogenation of hydrocarbons to be dehydrogenated and at least one jet pump.

* * * * *